United States Patent [19]

Gerszberg

[11] 4,308,206
[45] Dec. 29, 1981

[54] PROCESS FOR PREPARING DERIVATIVES OF 5,11-DIHYDRO-6H-PYRIDO[2,3-B][1,4]-BENZODIAZEPIN-6-ONE, AND THE FINAL DERIVATIVES AND SYNTHESIS INTERMEDIATES OBTAINED THEREBY

[75] Inventor: Szepsel Gerszberg, Buenos Aires, Argentina

[73] Assignee: Microsules Argentina S.A. de S.C.I.I.A., Buenos-Aires, Argentina

[21] Appl. No.: 149,560

[22] Filed: May 13, 1980

[30] Foreign Application Priority Data

Mar. 17, 1980 [IT] Italy .................. 20700 A/80

[51] Int. Cl.³ .......................................... C07D 471/04
[52] U.S. Cl. .......................................... 260/239.3 T
[58] Field of Search ................................ 260/239.3 T

[56] References Cited

U.S. PATENT DOCUMENTS

| | | | |
|---|---|---|---|
| 3,406,168 | 10/1968 | Schmidt | 260/239.3 T |
| 3,634,408 | 1/1972 | Schmidt et al. | 260/239.3 T |
| 3,660,380 | 5/1972 | Schmidt et al. | 260/239.3 T |
| 4,210,648 | 7/1980 | Schmidt et al. | 260/239.3 T |
| 4,213,984 | 7/1980 | Schmidt et al. | 260/239.3 T |
| 4,213,985 | 7/1980 | Schmidt et al. | 260/239.3 T |

FOREIGN PATENT DOCUMENTS

| | | |
|---|---|---|
| 1172943 | 6/1965 | Fed. Rep. of Germany ... 260/239.3 T |
| 1204680 | 5/1966 | Fed. Rep. of Germany ... 260/239.3 T |
| 1795183 | 7/1972 | Fed. Rep. of Germany ... 260/239.3 T |

OTHER PUBLICATIONS

Fieser and Fieser "Reagents for Organic Synthesis" (John Wiley and Sons, Inc.) (1961) p. 903.

*Primary Examiner*—Robert T. Bond
*Attorney, Agent, or Firm*—Cushman, Darby & Cushman

[57] ABSTRACT

This invention relates to a process for preparing derivatives of 5,11-dihydro-6H-pyrido[2,3-b][1,4]-benzodiazepin-6-one of general formula (I)

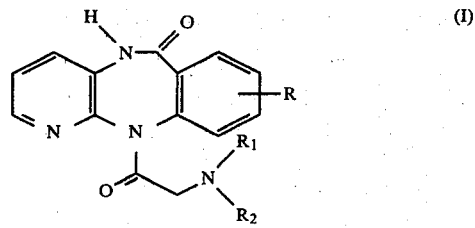

in which
R is hydrogen, halogen or methyl;
$R_1$ and $R_2$ are linear or branched $C_2$-$C_4$ alkyl groups, which alternatively may be joined together to give a piperazine cycle which can be substituted in position 4 with a methyl, ethyl or benzyl group, and their salts with organic and inorganic acids, characterised by comprising the following stages:

(a) reacting a compound of general formula (X),

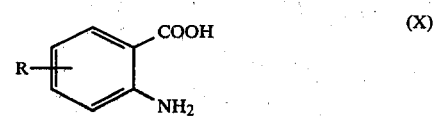

in which R has the meaning heretofore defined, with 2-cloro-3-amino-pyridine of formula (III)

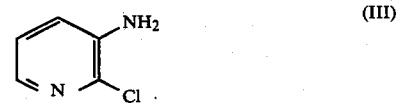

in the presence of polyphosphoric acid, to give an intermediate of general formula (II)

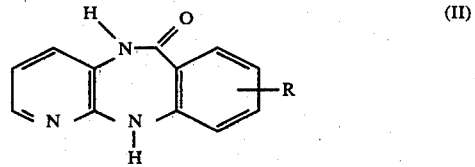

(b) reacting said intermediate with a compound of general formula (XI)

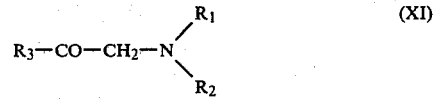

in which $R_1$ and $R_2$ have the meaning heretofore defined and $R_3$ is a hydroxyl or halogen, in an inert solvent at a maximum temperature equal to the solvent boiling point, to give said derivatives of general formula (I).

The invention also relates to the final compounds thus obtained, and the synthesis intermediates obtained during the course of said process.

The final products of formula (I) are of great interest in the pharemaceutical field.

11 Claims, No Drawings

PROCESS FOR PREPARING DERIVATIVES OF 5,11-DIHYDRO-6H-PYRIDO[2,3-B][1,4]-BENZODIAZEPIN-6-ONE, AND THE FINAL DERIVATIVES AND SYNTHESIS INTERMEDIATES OBTAINED THEREBY

This invention relates to a new process for preparing known derivatives of 5,11-dihydro-6H-pyrido[2,3-b][1,4]-benzodiazepin-6-one, of general formula (I)

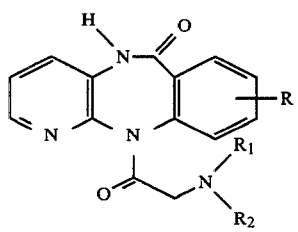

in which

R is H, halogen or $CH_3$;

$R_1$ and $R_2$ are linear or branched chain $C_2$-$C_4$ alkyl groups, which alternatively may be joined together to give a piperazine cycle which can be substituted in position 4 with a $CH_3$, $C_2H_5$ or benzyl group, and to the salts of said derivatives with organic and inorganic acids.

In the form of salts with organic and inorganic acids, the basic derivatives of general formula (I) possess properties which make them suitable for treating ulcers, and are therefore used for preparing drugs of considerable interest in this field.

German Pat. No. 1,179,943 patented June 10, 1965 describes the preparation of the basic compound of general formula (II)

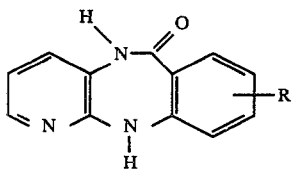

i.e. 5,11-dihydro-6H-pyrido[2,3-b][1,4]-benzodiazepin-6-one; the meaning of R in formula (II) is as defined heretofore. Said patent claims a process which proceeds by way of three stages: the first comprises reacting 2-chloro-3-amino-pyridine, of general formula (III)

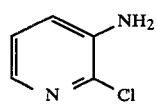

with substituted o-nitrobenzoic acid of general formula (IV)

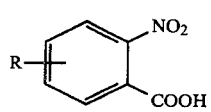

or with the corresponding acyl halide.

Condensation between (III) and (IV) is carried out in an inert solvent using equimolecular quantities of (III) and (IV). The liberated hydrochloric acid is fixed by adding a tertiary base such as triethylamine or pyridine, sodium carbonate or bicarbonate, or an excess of said compound (III). The reaction begins at ambient temperature and is completed at the reflux temperature of the solvent used. This produces 2-chloro-3 (2'-nitrobenzoylamino)-pyridine of general formula (V)

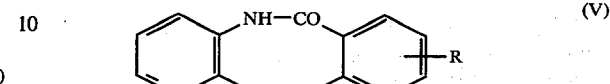

In the next stage, the nitro group is reduced to amine to give the compound of formula (VI)

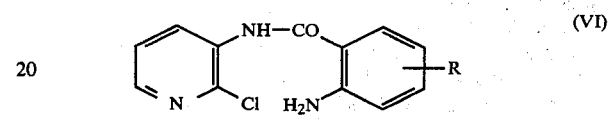

where R again has the meaning indicated heretofore. This reduction is carried out with Raney nickel at about 50° C. and 100 atmospheres, or with stannous chloride in the presence of an inorganic acid.

In the third and final stage, compound (VI) is cyclised to give said compound of formula (II), either by direct fusion at 200°–210° C., or in the presence of trichlorobenzene.

German Pat. No. 1,204,680 patented May 26, 1966 describes the preparation of position 5 derivatives of the compounds of said general formula (II), these derivatives not falling within the scope of the present invention.

German Auslegeschrift No. 1,795,183 published July 20, 1972 describes a process for synthesizing said compounds of general formula (I) starting from said compounds of general formula (II) prepared by the method of said German Pat. No. 1,179,943, or from their derivatives substituted in position 5. In German Pat. No. 1,795,183, these starting compounds (II) are reacted with a halide of general formula (VII)

wheren Al and Al', which may be equal or different, are chlorine, bromine or iodine.

The reaction is carried out in aromatic hydrocarbons or ethers at their boiling point in the presence of a base in order to block the liberated acid (triethylamine, pyridine, sodium carbonate or bicarbonate). This produces the compound of general formula (VIII), i.e. 11-haloacetyl-5,11-dihydro-6H-pyrido[2,3-b][1,4]-benzodiazepin-6-one

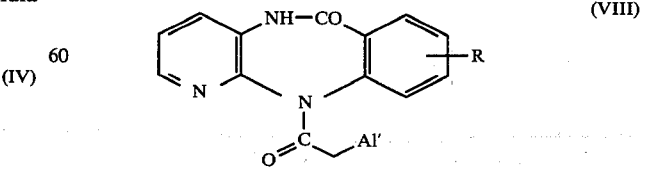

where R and Al' have the meaning heretofore stated.

Finally, said compounds of formula (VIII) are reacted with amines of general formula (IX)

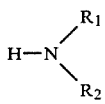

where $R_1$ and $R_2$ have the meaning heretofore defined, to give the initially described compounds of general formula (I).

This latter reaction takes place in solvents such as ethanol, acetone, dioxane or aromatic hydrocarbons, in the presence of an excess of amine in order to fix the liberated hydracid.

It can therefore be stated that, up to the present time, it has been known to prepare compounds of general formula (I) by a process consisting overall of five successive stages, as described in the two said German Pat. Nos. 1,179,943, which teaches the preparation of the intermediates of general formula (II), and 1,795,183, which teaches the synthesis of the final compounds (I) starting from said intermediates.

This therefore represents a synthesis process which proceeds by way of a sequence of passages which can be defined as linear. In a synthesis of this kind, the yield of final product is known to decrease rapidly with the increase in the number of linear passages, in that there is a loss of intermediates at each passage, this becoming more serious and undesirable as the synthesis proceeds due to the fact that the corresponding intermediates gradually become more valuable.

The object of the present invention is to prepare said compounds of general formula (I) in such a manner as to obviate the aforesaid problem of the known art, and thus to propose a synthesis which is substantially more economical and has an improved final product yield than the known method.

To attain this object, according to the present invention, a synthesis is proposed which is not of linear type such as that taught by the aforesaid known art, but is of convergent type in that two basic intermediates are obtained by independent paths, each comprising a single passage, the subsequent condensation of the two intermediates giving the final desired product such as to obtain an overall synthesis comprising a substantially small number of passages, thus reducing the loss of the most valuable intermediates formed in the synthesis.

This object is attained according to the present invention by a process for preparing derivatives of 5,11-dihydro-6H-pyrido [2,3-b][1,4]-benzodiazepin-6-one of general formula (I)

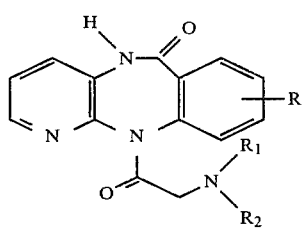

in which
R is hydrogen, halogen or methyl;
$R_1$ and $R_2$ are linear or branched $C_2$–$C_4$ alkyl groups, which alternatively may be joined together to give a piperazine cycle which can be substituted in position 4 with a methyl, ethyl or benzyl group,
and their salts with organic and inorganic acids, characterised by comprising the following stages:

(a) reacting a compound of general formula (X)

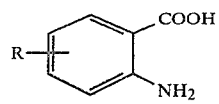

in which R has the meaning heretofore defined, with 2-chloro-3-amino-pyridine of formula (III)

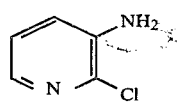

in the presence of polyphosphoric acid, to give an intermediate of general formula (II)

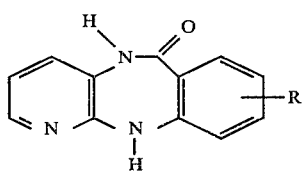

(b) reacting said intermediate with a compound of general formula (XI)

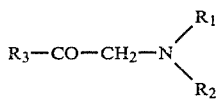

in which $R_1$ and $R_2$ have the meaning heretofore defined, and $R_3$ is a hydroxyl or halogen, in an inert solvent at a maximum temperature equal to the solvent boiling point, to give said derivatives of general formula (I).

According to one embodiment of the invention, the reaction of stage (a) is carried out at a temperature chosen between about 160° and 200° C., to give said intermediate of formula (II).

According to a further embodiment of the process of the invention, the reaction of stage (a) is carried out at a temperature chosen between about 90° and 130° C., to give a compound of formula (VI)

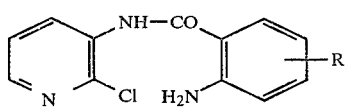

this compound being then converted into said intermediate of formula (II) before proceeding in accordance with said stage (b).

Said compound of general formula (VI) is converted into the corresponding intermediate of formula (II) by raising the reaction temperature of said stage (a) to about 160° to 200° C.

In a further embodiment of the process according to the invention, said compound of general formula (VI) is isolated from the reaction medium of said stage (a) before proceeding in accordance with said stage (b).

The reaction according to said stage (b) can be carried out by adding said compound of general formula (XI) to the reaction mixture of said stage (a).

Alternatively, said intermediate of general formula (II) obtained from said stage (a) is isolated, and then subjected to the reaction of said stage (b) with said compound of general formula (XI) in which $R_3$ is a halogen. In this case, a base is used in the reactin of said stage (b), chosen from organic compounds such as triethylamine or pyridine, or inorganic compounds such as sodium carbonate or bicarbonate.

The present invention also relates to the final compounds of general formula (I) prepared by said process according to the invention, and to said synthesis intermediates of general formula (II) and (VI) obtained during the course of said process.

Describing in greater detail the process substantially defined heretofore, if it is required to obtain an intermediate of general formula (II) then the reaction of said stage (a) is carried out in polyphosphoric acid (PPA) at high temperature, about 160°–200° C., as this favours the complete ring closure of the structure of the compound of formula (VI) through which the reaction proceeds.

On the other hand, if it is required to isolate said compound of formula (VI), the reaction of said stage (a) is carried out at a lower temperature (90°–130° C.), which does not cause closure of the cyclic system (VI).

The substituted glycine compounds of said general formula (XI) can be prepared from the corresponding amines of general formula (IX)

(IX)

by reaction with monochloracetic acid or an ester thereof, the preparation of which is described for example in the following literature:

U.S. Pat. No. 3,457,302 (C.A. 71, 91869 v(1969)); S. Sakakibara and M. Itoh, Bull. Chem. Soc. Japan 40 (3), 656 (1967); A. Nudelman, R. J. McCaully and S. C. Bell, J. Pharm. Sci. 63 (12), 1880 (1974); O. Hromatka, W. Graf and M. Knollmüller, Monath. 97 (1), 19 (1966).

The reaction of said stage (b) can be carried out directly in the same reaction medium as used for preparing the compound of formula (II), without the need to isolate this latter, by adding the glycine derivative of formula (XI) to the reaction mixture of said stage (a).

This gives a one pot synthesis. However, if the intermediate compound (II) is isolated, the amidation reaction of said stage (b) is carried out by using a glycine derivative of formula (XI) in which $R_3$ is a halogen, in an inert solvent in the presence of a base in order to fix the hydracid which evolves, at a temperature generally equal to the boiling point of the solvent. This latter can be benzene or toluene, and the base used can be organic, such as triethylamine and pyridine, or inorganic such as sodium carbonate or bicarbonate.

Some detailed non-limiting embodiments are given hereinafter for the purpose of better describing the process according to the present invention.

EXAMPLE 1

2-chloro-3-(2'-amino-4'-chlorobenzoylamino)-pyridine 20 g (0.155 moles) of 3-amino-2-chloropyridine, 26.7 g (0.155 moles) of 4-chloro-anthranilic acid, and 140 g of polyphosphoric acid are placed in a two neck flask fitted with a thermometer and mechanical stirrer.

Heating is commenced, and stirring is started at 60°. Heating is continued until an internal temperature of 100°–120° is reached, and the course of the reaction is followed by thin layer chromatography. This temperature is maintained for 1.5 hours.

When the reaction is finished, the mixture is cooled to 80° and poured while stirring into 500 cc of water. The mixture is neutralised with 40% sodium hydroxide solution, and the precipitate obtained is filtered. It is washed by remixing with cold ethanol and is recrystallised from this solvent. A product having a melting point of 198°–202° is obtained.

EXAMPLE 2

5,6-dihydro-6-oxo-8-methyl-11H-pyrido[2,3-b][1,4]benzodiazepine 40 g (0.310 moles) of 3-amino-2-chloropyridine, 46.8 g (0.310 moles) of 5-methylanthranilic acid and 280 g of polyphosphoric acid are placed in a two neck flask fitted with a thermometer and mechanical stirrer.

It is heated to an internal temperature of 170°–190°. The resultant brown viscous solution is kept under continuous stirring, giving rise to the formation of foam and evolving hydrochloric acid.

Within 20–30 minutes the foam disappears, and the mixture is kept at the same temperature for about one hour. The course of the reaction is followed by thin layer chromatography, and when it is finished it is poured while stirring into 1 litre of water after previously being cooled to 90°.

It is filtered, and after washing with sufficient water and drying, the crude product is extracted with chloroform, decolorised with activated carbon, and filtered. The solution is evaporated under vacuum, and the residue is dissolved in ethanol, from which yellow needles having a melting point of 255°–260° crystallise out.

EXAMPLE 3

11-[(4'-methylpiperazino)acetyl]-5,11-dihydro-6H-pyrido[2,3-b][1,4]benzodiazepin-6-one 40 g (0.310 moles) of 3-amino-2-chloropyridine, 42.4 g (0.310 moles) of anthranilic acid, and 280 g of polyphosphoric acid are placed in a two neck flask fitted with a thermometer and mechanical stirrer. Heating is commenced, and stirring is begun when a temperature of 60° is reached. Heating is continued until an internal temperature of 170°–190° is reached. Under these conditions, a very viscous brown solution is present, and hydrochloric acid is evolved with the formation of foam. This disappears within 30 minutes.

The solution is kept stirred at this temperature for about 1 hour. The end of the reaction is determined by thin layer chromatography.

The temperature of the reaction mixture is then lowered to 90°–100°, and 15.8 g of 4-methyl-1-piperazinacetic acid are incorporated, maintaining this temperature for two hours under stirring. The termination of the reaction is determined by the corresponding chromatograph check.

The solution is poured into 300 cc of water, and neutralised with concentrated ammonia.

The resultant precipitate is filtered and dried. The crude product is dissolved in 250 cc of isopropanol, and 20 cc of hydrochloric isopropanol (28%) are incorporated, to precipitate a product of white cream colour. Recrystallisation from isopropanol gives the dihydrochloride of the product indicated in the title, which has a melting point of 251°–256° (decomposition) (corrected).

EXAMPLE 4

(a)
5,6-dihydro-6-oxo-11H-pyrido[2,3-b][1,4]benzodiazepine

The preparation indicated in example 3 is repeated, and after the cyclising reaction is completed by heating to 170°–190° in polyphosphoric acid, the reaction mixture is cooled to 120°, and is poured under stirring into 2.750 litres of water at ambient temperature. Most of the product then precipitates. The pH is adjusted to 7–7.5, with a 40% sodium hydroxide solution to complete precipitation and change the structure of the precipitate. The mixture must be cooled during neutralisation.

It is filtered immediately and the precipitate is washed on the filter with water, drying the mother liquors. The dry crude product is taken up in 200 cc of boiling chloroform, and decolorised with activated carbon. After heating under reflux for 10 minutes, the mixture is filtered. Most of the chloroform is removed by distillation, ethanol is added, and the last traces of chloroform are eliminated by azeotropic distillation. The solution is cooled at ambient temperature, and the soid obtained is filtered and washed by resuspending in cold ethanol (60 cc twice). Yellowish needles are obtained having a melting point of 284°–286°.

(b)
11-[(4'-methylpiperazino)acetyl]-5,11-dihydro-6H-pyrido [2,3-b][1,4]benzodiazepin-6-one 100 cc of anhydrous toluene, 10.55 g (0.05 moles) of 6-oxo-5,6-dihydro-11H-pyrido[2,3-b][1,4]benzodiazepine, and 10.59 g (0.06 moles) of 4-methyl-1-piperazinacetyl chloride are placed in a three neck flask fitted with a condenser comprising a calcium chloride tube, a stirrer and decanter.

4.1 g (3.6 cc) of triethylamine dissolved in 15 cc of anhydrous toluene are fed continuously drop by drop.

Heating is commenced, and the mixture is kept at 80° for about three hours. The course of the reaction is followed by thin layer chromatography. When the reaction is finished, the mixture is cooled to ambient temperature and washed with water (50 cc twice), throwing away the aqueous phase. The toluene phase is dried and decolorised with activated carbon. Most of the toluene is removed by distillation under vacuum, isopropanol is added and the mixture distilled azeotropically to eliminate traces of toluene. 3.5 cc of hydrochloric isopropanol (38%) and 45 cc of isopropanol are then added, to precipitate the dihydrochloride of 11-[(4'-methylpiperazino)acetyl]-5,11-dihydro-6H-pyrido[2,3-b][1,4]benzodiazepin-6-one. The crude product is filtered off and is recrystallised from isopropanol, to give a white product having a melting point of 252°–256° (decomposition) (corrected).

From the foregoing description, it is apparent that the process according to the present invention consists of a convergent synthesis for the products of general formula (I), i.e. in said stage (a) a first intermediate is prepared (compound of general formula (II)), which, in order to give the final product, is reacted with a second intermediate (glycine compound of general formula (XI)) prepared separately and independently of the synthesis of the intermediate (II).

This gives the substantial advantage of providing two intermediates which give the final product by condensation, these intermediates being prepared by a single synthesis passage, so avoiding the inevitable compound loss and thus quantitative yield reduction which are typical of the linear synthesis proposed by the aforesaid known art.

The process according to the invention allows the final product (I) to be obtained by a number of passages (at the most three) which is certainly less than the number in the process proposed by the said German patents, thus giving the clear advantage of an economical preparation process.

The invention therefore advantageously attains the stated objects.

I claim:

1. A process for preparing a 5,11-dihydro-6H-pyrido (2,3-b) (1,4)-benzodiazepin-6-one of the formula (I)

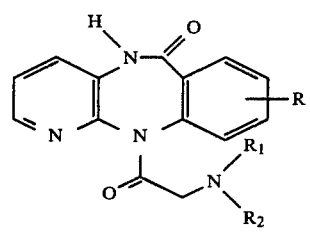

in which
R is hydrogen, halogen or methyl;
R₁ and R₂ are linear or branched C₂–C₄ alkyl groups, which alternatively may be joined together to give a piperazine cycle which can be substituted in position 4 with a methyl, ethyl or benzyl group, and their salts with organic and inorganic acids, said process comprising the steps of:
(a) reacting a compound of the formula (X)

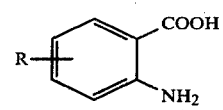

in which R has the meaning defined above, with 2-chloro-3-amino-pyridine of the formula (III)

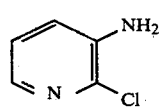

in the presence of polyphosphoric acid, to give an intermediate of the formula (II)

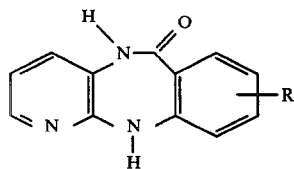

(b) reacting said intermediate with a compound of the formula (XI)

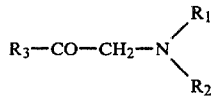

in which $R_1$ and $R_2$ have the meaning heretofore defined, and $R_3$ is a hydroxyl or halogen, in an inert solvent at a maximum temperature equal to the solvent boiling point, to give the compound of formula (I).

2. A process as claimed in claim 1, wherein the reaction of step (a) is carried out at a temperature between about 160° and 200° C., to give said intermediate of formula (II).

3. A process as claimed in claim 1, wherein the reaction of step (a) is carried out at a temperature between about 90° and 130° C., to give a compound of the formula (VI)

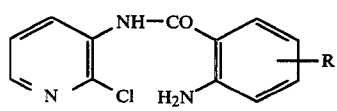

said compound then being converted into said intermediate of formula (II) before proceeding in accordance with step (b).

4. A process as claimed in claim 3, wherein said compound of formula (VI) is converted into the corresponding intermediate of formula (II) by raising the reaction temperature of step (a) to between about 160° and 200° C.

5. A process as claimed in claim 3, wherein said compound of formula (VI) is isolated from the reaction medium of step (a) before operating in accordance with step (b).

6. A process as claimed in claim 1, wherein the reaction in accordance with step (b) is carried out by adding said compound of formula (XI) to the reaction mixture of step (a).

7. A process as claimed in claim 1, wherein said intermediate of formula (II), prepared in accordance with step (a) is isolated and is then subjected to the reaction of step (b) with a compound of formula (XI) in which $R_3$ is a halogen, in the presence of a base arranged to fix the hydracid which is evolved.

8. The process as claimed in claim 1 consisting essentially of steps (a) and (b).

9. The process as claimed in claim 7, wherein the base is triethylamine, pyridine, sodium carbonate or sodium bicarbonate.

10. The process as claimed in claim 1, wherein the compounds of formula (I) are prepared in the form of the free base.

11. A process for preparing a 5,11-dihydro-6H-pyrido (2,3-b) (1,4)-benzodiazepin-6-one of the formula (I)

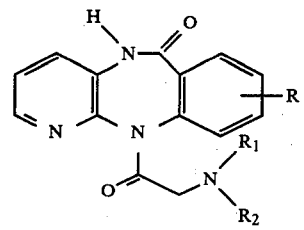

wherein R is hydrogen, halogen or methyl; $R_1$ and $R_2$ are linear or branched $C_2$-$C_4$ alkyl groups, which alternatively may be joined together to give a piperazine cycle which can be substituted in position 4 with a methyl, ethyl or benzyl group, said process consisting essentially of the following steps:

(a) reacting a compound of the formula (X)

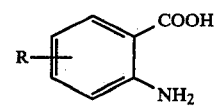

in which R has the meaning defined above, with 2-chloro-3-amino pyridine of the formula (III)

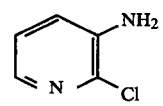

in the presence of polyphosphoric acid, to give an intermediate of the formula (II)

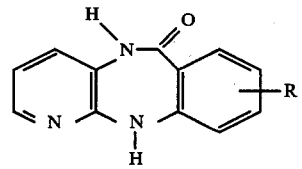

and (b) reacting said intermediate with a compound of the formula (XI)

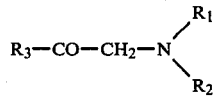

wherein $R_1$ and $R_2$ have the meaning defined above, and $R_3$ is a hydroxyl or halogen, in an inert solvent at a maximum temperature equal to the solvent boiling point, to give the compound of formula (I).

* * * * *